United States Patent
Eggen et al.

(10) Patent No.: US 12,409,313 B2
(45) Date of Patent: Sep. 9, 2025

(54) THERMAL STIMULATION AND SUBSEQUENT COOLING FOR FULLY IMPLANTABLE LVAD CONTROLLER

(71) Applicant: Boston Scientific Scimed, Inc., Maple Grove, MA (US)

(72) Inventors: Michael D. Eggen, Chicago City, MN (US); Yong K. Cho, Excelsior, MN (US); Avram Scheiner, Vadnais Heights, MN (US); Ramesh Raghupathy, New Brighton, MN (US); Thomas W. Radtke, Ramsey, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1177 days.

(21) Appl. No.: 16/935,433

(22) Filed: Jul. 22, 2020

(65) Prior Publication Data
US 2022/0023515 A1 Jan. 27, 2022

(51) Int. Cl.
| | |
|---|---|
| *A61M 60/00* | (2021.01) |
| *A61M 60/135* | (2021.01) |
| *A61M 60/50* | (2021.01) |
| *A61F 7/00* | (2006.01) |
| *A61F 7/08* | (2006.01) |
| *A61F 7/10* | (2006.01) |

(52) U.S. Cl.
CPC .......... *A61M 60/50* (2021.01); *A61M 60/135* (2021.01); *A61F 2007/0011* (2013.01); *A61F 7/08* (2013.01); *A61F 7/10* (2013.01); *A61M 2205/18* (2013.01); *A61M 2205/3372* (2013.01); *A61M 2205/3584* (2013.01); *A61M 2205/3606* (2013.01); *A61M 2205/50* (2013.01); *A61M 2205/8206* (2013.01); *A61M 2230/50* (2013.01)

(58) Field of Classification Search
None
See application file for complete search history.

(56) References Cited

U.S. PATENT DOCUMENTS

| | | | |
|---|---|---|---|
| 6,176,822 B1 * | 1/2001 | Nix | ..................... A61M 60/816 623/3.1 |
| 7,997,854 B2 | 8/2011 | LaRose et al. | |
| 8,419,609 B2 | 4/2013 | Shambaugh, Jr. et al. | |
| 8,617,230 B2 | 12/2013 | Diller et al. | |
| 9,549,844 B2 | 1/2017 | Diller et al. | |
| 9,882,420 B2 | 1/2018 | Cong et al. | |
| 10,554,069 B2 | 2/2020 | Paralikar et al. | |
| 10,556,050 B2 | 2/2020 | Begg et al. | |

(Continued)

OTHER PUBLICATIONS

International Search Report and Written Opinion of International Application No. PCT/US2021/039363, dated Sep. 17, 2021, 16 pp.

(Continued)

*Primary Examiner* — Sana Sahand
(74) *Attorney, Agent, or Firm* — Seager, Tufte & Wickhem LLP

(57) ABSTRACT

A method of cooling a mammal with an implantable blood pump. The method includes measuring a temperature of an internal controller, the internal controller being in communication with the implantable blood pump. an alert is generated if the temperature of the internal controller exceeds a predetermined temperature threshold.

20 Claims, 3 Drawing Sheets

(56) References Cited

U.S. PATENT DOCUMENTS

| | | |
|---|---|---|
| 10,624,551 B2 | 4/2020 | Bardy et al. |
| 2002/0111533 A1* | 8/2002 | Melvin ................ A61F 2/2481 623/3.1 |
| 2005/0075696 A1* | 4/2005 | Forsberg ........... H02J 7/007192 607/61 |
| 2006/0178617 A1* | 8/2006 | Adams ................ A61B 5/0028 128/903 |
| 2008/0319544 A1* | 12/2008 | Yaegashi ............. A61M 60/178 623/3.28 |
| 2013/0178915 A1 | 7/2013 | Radziemski et al. |
| 2015/0038771 A1* | 2/2015 | Marseille .............. G16H 40/63 600/16 |
| 2017/0281435 A1 | 10/2017 | Diller et al. |
| 2018/0125703 A1 | 5/2018 | Diller |
| 2018/0126177 A1* | 5/2018 | Scott .................... A61F 7/0085 |
| 2018/0207027 A1 | 7/2018 | Diller et al. |
| 2018/0280620 A1* | 10/2018 | Reichthalhammer ....................... A61M 5/16877 |
| 2018/0338857 A1 | 11/2018 | Diller et al. |
| 2019/0336767 A1* | 11/2019 | Klepfer ................ A61N 1/3987 |
| 2020/0101298 A1 | 4/2020 | Ellingson et al. |
| 2020/0121187 A1 | 4/2020 | Sarkar et al. |
| 2021/0408843 A1* | 12/2021 | Roberts ................... H04B 5/79 |

OTHER PUBLICATIONS

Carlisle et al., "The Effects of Heating and Cooling the Spinal Cord and Hypothalamus on Thermoregulatory Behaviour in the Pig," The Journal of Physiology, vol. 231, No. 2, Jun. 1973, pp. 353-364.

* cited by examiner

THERMAL STIMULATION AND SUBSEQUENT COOLING FOR FULLY IMPLANTABLE LVAD CONTROLLER

CROSS-REFERENCE TO RELATED APPLICATION n/a.

FIELD

The present technology is generally related to a method and system of thermally stimulating a patient with an implantable controller for an implantable blood pump.

BACKGROUND

With the advent of fully implantable blood pump systems comes a controller that is implanted within the body of patient. The controller has an internal battery that provides power to the implantable blood pump. Like any controller with a battery, the controller gives off heat as it provides power to the pump. As the power increases, for example, in the presence of thrombus, more heat is transferred from the controller to the patient, which may cause discomfort and even pain.

SUMMARY

The techniques of this disclosure generally relate to a method and system of thermally stimulating a patient with an implantable controller for an implantable blood pump.

In one aspect, the present disclosure provides a method of cooling a patient with an implantable blood pump. The method includes measuring a temperature of an internal controller, the internal controller being in communication with the implantable blood pump. An alert is generated if the temperature of the internal controller exceeds a predetermined temperature threshold.

In another aspect of this embodiment, the alert instructs the patient to place a heating pad on a body of the patient.

In another aspect of this embodiment, the alert instructs the patient to place the heating pad on the back of a neck of the body of the patient.

In another aspect of this embodiment, wherein the alert instructs the patient to go to a hospital.

In another aspect of this embodiment, the predetermined temperature threshold is 39 degrees Celsius.

In another aspect of this embodiment, the predetermined temperature threshold is between 39 degrees Celsius and 43 degrees Celsius.

In another aspect of this embodiment, the predetermined temperature threshold is 43 degrees Celsius.

In another aspect of this embodiment, the method further includes communicating the measured temperature to an external controller in communication with the internal controller.

In another aspect of this embodiment, the alert is generated by the external controller.

In another aspect of this embodiment, the alert instructs the patient to thermally stimulate the back of a neck of the body of the patient.

In one aspect, a system for cooling a patient with an implantable blood pump includes an internal controller configured to be in communication with the implantable blood pump. An external controller is configured to be in communication with the internal controller, the external controller being configured to generate an alert if a temperature of the internal controller exceeds a predetermined temperature threshold.

In another aspect of this embodiment, the internal controller includes at least one temperature sensor configured to measure a temperature of the internal controller.

In another aspect of this embodiment, the internal controller is configured to communicate the measured temperature to the external controller.

In another aspect of this embodiment, the alert instructs the patient to place the heating pad on the back of a neck of the body of the patient.

In another aspect of this embodiment, the alert instructs the patient to go to a hospital.

In another aspect of this embodiment, the predetermined temperature threshold is 39 degrees Celsius.

In another aspect of this embodiment, the predetermined temperature threshold is between 39 degrees Celsius and 43 degrees Celsius.

In another aspect of this embodiment, the predetermined temperature threshold is 43 degrees Celsius.

In another aspect of this embodiment, the alert instructs the patient to thermally stimulate the back of a neck of the body of the patient.

In one aspect, a method of cooling a patient with an implantable blood pump includes measuring a temperature of an internal controller with a temperature sensor coupled to the internal controller, the internal controller being in communication with the implantable blood pump. The measured temperature is communicated to an external controller in communication with the internal controller. An alert is generated if the temperature of the internal controller exceeds a temperature greater than 39 degrees Celsius, the alert notifying the patient to thermally stimulate a back of the neck of the patient.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 1:
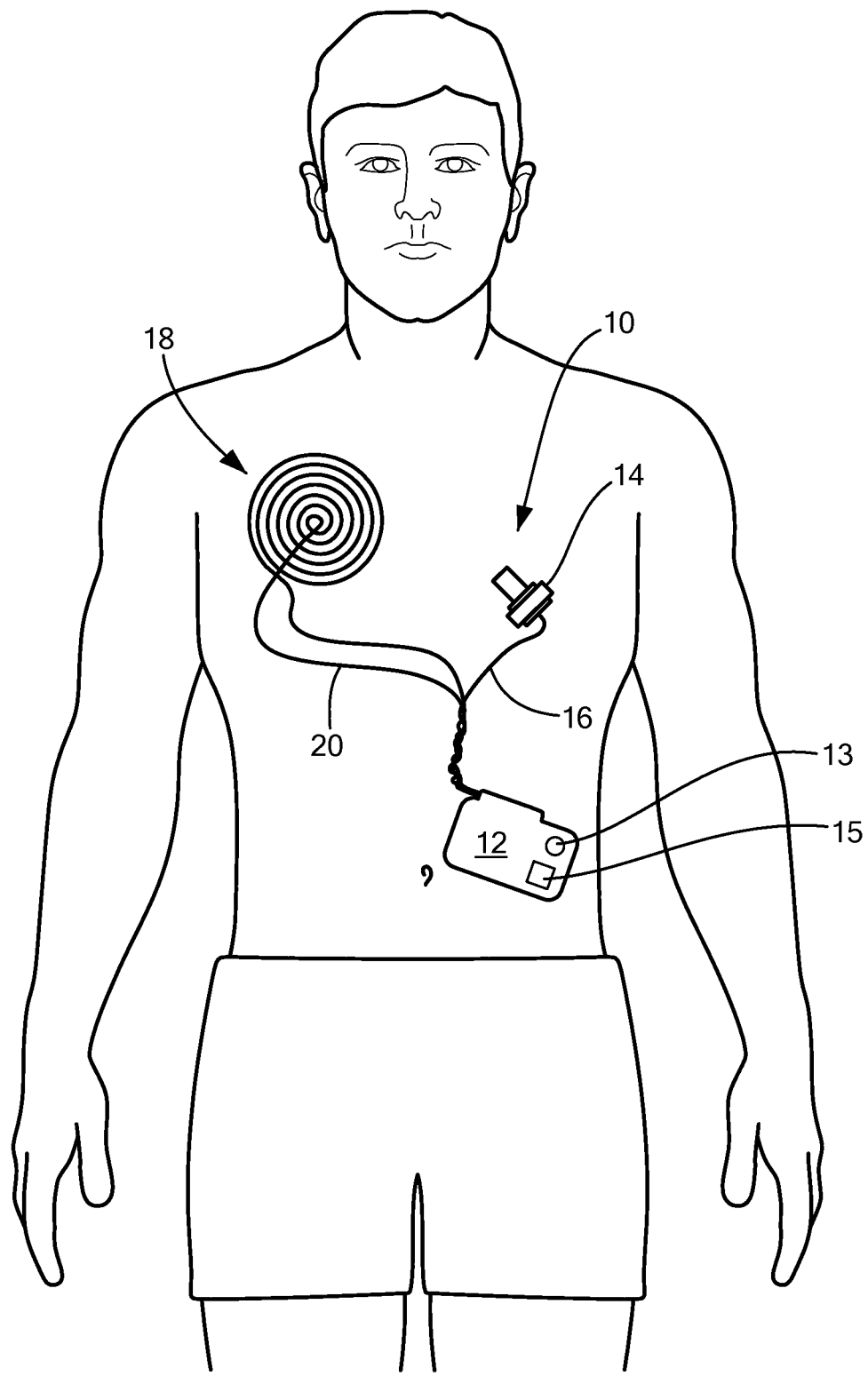
FIG. 1 is an internal system view of an implantable blood pump with a TETS receiver source constructed in accordance with the principles of the present application.
Figure 2:
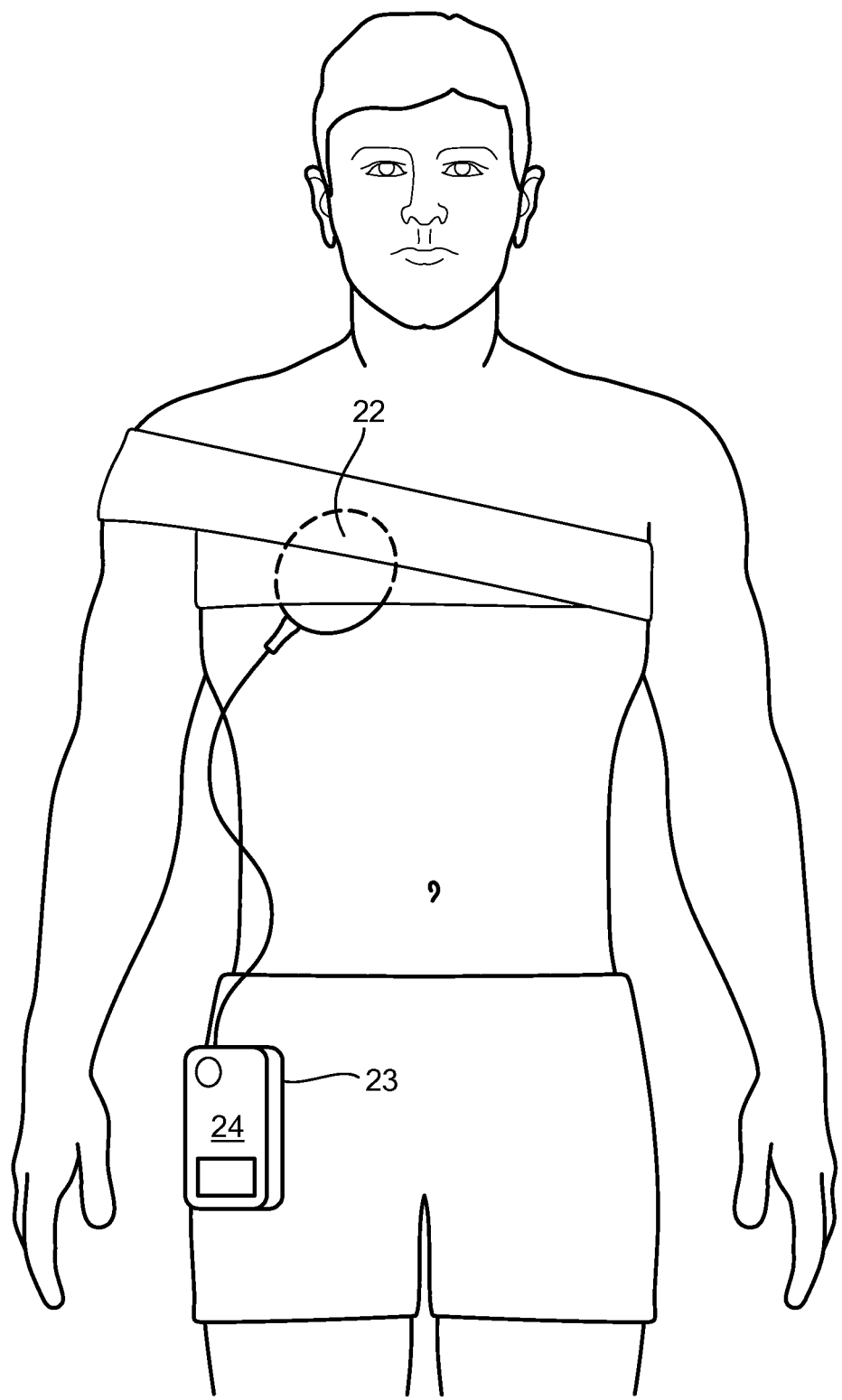
FIG. 2 is an external view of a TETS transmitter and a controller of the system shown in FIG. 1.

Referring now to the drawings in which like reference designators refer to like elements there is shown in FIGS. 1 and 2 an exemplary mechanical circulatory support device (MCSD) constructed in accordance with the principles of the present application and designated generally as "10." The MCSD 10 may be fully implantable within a patient, whether human or animal, which is to say there are no percutaneous connections between the implanted components of the MCSD 10 and the components outside of the body of the patient. In the configuration shown in FIG. 1, the MCSD 10 includes an internal controller 12 implanted within the body of the patient. The internal controller 12 includes a control circuit having processing circuitry configured to control operation of an implantable blood pump 14. The internal controller 12 may include an internal power source 13, configured to power the components of the controller and provide power to one or more implantable medical devices, for example, the implantable blood pump, such as a ventricular assist device ("VAD") 14 implanted within the left ventricle of the patient's heart. The power source 13 may include a variety of different types of power sources including an implantable battery. The internal controller 12 may also include one or more temperature sensors 15 configured to measure a temperature of the controller 12 during operation of VAD 14. VADs 14 may include centrifugal pumps, axial pumps, or other kinds electromagnetic pumps configured to pump blood from the heart to blood vessels to circulate around the body. One such centrifugal pump is the HVAD and is shown and described in U.S. Pat. No. 7,997,854, the entirety of which is incorporated by reference. One such axial pump is the MVAD and is shown and described in U.S. Pat. No. 8,419,609, the entirety of which is incorporated herein by reference. In an exemplary configuration, the VAD 14 is electrically coupled to the internal controller 12 by one or more implanted conductors 16 configured to provide power to the VAD 14, relay one or more measured feedback signals from the VAD 14, and/or provide operating instructions to the VAD 14.

Continuing to refer to FIG. 1, a receiving or internal coil 18 may also be coupled to the internal controller 12 by, for example, one or more implanted conductors 20. In an exemplary configuration, the receiving coil 18 may be implanted subcutaneously proximate the thoracic cavity, although any subcutaneous position may be utilized for implanting the receiving coil 18. The receiving coil 18 is configured to be inductively powered through the patient's skin by a transmission or external coil 22 (seen in FIG. 2) disposed opposite the receiving coil 18 on the outside/exterior of the patient's body. For example, as shown in FIG. 2, a transmission coil 22 may be coupled to an external controller 23 having a power source 24, for example, a portable battery carried by the patient or wall power. In one configuration, the battery is configured to generate a radiofrequency signal for transmission of energy from the transmission coil 22 to the receiving coil 18. The receiving coil 18 may be configured for transcutaneous inductive communication with the transmission coil 22.

Figure 3:
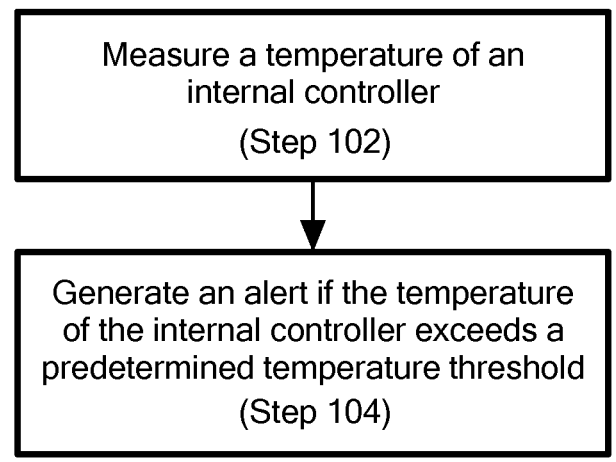
FIG. 3 is a flow chart showing the steps of an exemplary method of the present application.

Referring now to FIG. 3, in which a method of cooling a patient with pump 14 and controller 12 is shown. The method includes measuring a temperature of the internal controller 12 (Step 102). For example, the controller 12 may include the one or more temperature sensors 15 configured to measure a temperature of the controller 12. As more power to the pump 14 is required, the temperature of the controller 12 may increase beyond a predetermined temperature threshold. If the temperature of the internal controller 12 exceeds the predetermined temperature threshold an alert may generated that instructs the patient, whether human or animal, with the implanted pump 14 to thermally stimulate a portion of the patient's body (Step 104). For example, the alert may instruct the patient to apply a heating pad to the back of the neck, which has the effect of cooling the body. In particular, a heating pad or thermal stimulus at a temperature of 42-44 degrees Celsius placed on the back of the neck may reduce the patient's core temperature by approximately 2 degrees Celsius. This may reduce the temperature of the controller 12 by 33% if heated 6 degrees Celsius for example, and allows time for the patient to get to the hospital, while minimizing thermal tissue damage and pain. In other configurations, the alert may instruct the user to bring cold fluids, to place a cold vest on the body, or other methods to cool the body. In an exemplary configuration, the internal controller 12 communicates with the external controller 23 which generates the alert. For example, the internal controller 12 may commutate via wireless communication, for example, Bluetooth, with the external controller 23 concerning the measured temperature. The alert may be an audio or text alert that notifies the patient of either the overheated controller 12 or with a specific instruction to cool the patient's body and/or to go to a hospital or see a clinician. Exemplary temperature thresholds may be 2 degrees Celsius above body temperature, between 2 and 7 degrees Celsius above body temperature, or 7 degrees Celsius above body temperature.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A system comprising:
   an internal controller including a control circuit having processing circuitry, the internal controller configured to be implanted within a patient and configured to be in communication with an implantable blood pump; and
   an external controller configured to be in communication with the internal controller and configured to determine a temperature of the internal controller, the external controller being configured to generate an alert if the temperature of the internal controller exceeds a predetermined temperature threshold.

2. The system of claim 1, wherein the internal controller includes at least one temperature sensor configured to measure the temperature of the internal controller.

3. The system of claim 2, wherein the internal controller is configured to communicate the measured temperature to the external controller, and wherein the external controller is configured to determine the temperature of the internal controller by at least receiving the measured temperature from the internal controller.

4. The system of claim 1, wherein the alert instructs the patient with the implantable blood pump to place a heating pad on a back of a neck of a body of the patient.

5. The system of claim 1, wherein the alert instructs the patient with the implantable blood pump to go to a hospital.

6. The system of claim 1, wherein the predetermined temperature threshold is 39 degrees Celsius.

7. The system of claim 1, wherein the predetermined temperature threshold is between 39 degrees Celsius and 43 degrees Celsius.

8. The system of claim 1, wherein the predetermined temperature threshold is 43 degrees Celsius.

9. The system of claim 1, wherein the alert instructs the patient with the implantable blood pump to thermally stimulate a back of a neck of a body of the patient.

10. The system of claim 1, wherein the internal controller is physically separate from the implantable blood pump and is configured to control an operation of the implantable blood pump.

11. A system comprising:
an internal controller configured to be implanted within a patient and configured to be in communication with an implantable blood pump;
a temperature sensor coupled to the internal controller, the temperature sensor physically separate from the blood pump; and
an external controller configured to be in communication with the internal controller and configured to determine a temperature of the internal controller, the external controller being configured to generate an alert if the temperature of the internal controller exceeds a predetermined temperature threshold.

12. The system of claim 11, wherein the alert instructs the patient with the implantable blood pump to place a heating pad on a back of a neck of a body of the patient.

13. The system of claim 11, wherein the alert instructs the patient with the implantable blood pump to go to a hospital.

14. The system of claim 11, wherein the predetermined temperature threshold is 39 degrees Celsius.

15. The system of claim 11, wherein the predetermined temperature threshold is between 39 degrees Celsius and 43 degrees Celsius.

16. The system of claim 11, wherein the predetermined temperature threshold is 43 degrees Celsius.

17. The system of claim 11, wherein the alert instructs the patient with the implantable blood pump to thermally stimulate a back of a neck of a body of the patient.

18. The system of claim 11, wherein the blood pump is electrically coupled to the internal controller by one or more implanted conductors.

19. The system of claim 11, wherein the internal controller is coupled to an internal coil.

20. The system of claim 19, wherein the internal coil is configured to be inductively powered by an external coil.

* * * * *